United States Patent
Larsson et al.

(10) Patent No.: US 6,689,170 B1
(45) Date of Patent: Feb. 10, 2004

(54) IMPLANT ELEMENT

(76) Inventors: Cecilia Larsson, Brödragatan 26, S-412 74 Göteborg (SE); Peter Thomsen, Hängestensvägen 2, S-421 67, Göteborg (SE)

(*) Notice: Subject to any disclaimer, the term of this patent is extended or adjusted under 35 U.S.C. 154(b) by 0 days.

(21) Appl. No.: 09/423,250
(22) PCT Filed: May 14, 1998
(86) PCT No.: PCT/SE98/00891
§ 371 (c)(1),
(2), (4) Date: Feb. 14, 2000
(87) PCT Pub. No.: WO98/51231
PCT Pub. Date: Nov. 19, 1998

(30) Foreign Application Priority Data

May 16, 1997 (SE) ............................................. 9701872

(51) Int. Cl.[7] .................................................. A61F 2/36
(52) U.S. Cl. .................................. 623/23.53; 623/16.11
(58) Field of Search ............................. 623/23.55, 23.5, 623/23.53, 11.11–23.76, 1.1–6.64

(56) References Cited

U.S. PATENT DOCUMENTS 5,152,993 A * 10/1992 Bjursten et al. ............ 424/422
5,354,390 A    10/1994 Haszmann et al.

FOREIGN PATENT DOCUMENTS

GB    0676179    10/1995

OTHER PUBLICATIONS

C. Larson, et al. "Bone response to surface–modified titanium implants: studies on the early tissue response to machined and electropolished implants with different oxide thickness," *Biomaterials* 17 1996; pp. 605–615.

C. Larson, et al. "Bone response to surface–modified titanium implants: studies on the early tissue response to machined and electropolished implants with different oxide thickness," *Biomaterials* 15 1994; pp. 1062–1074.

D.M. Brunette, PhD, "The Effects of Implant Surface Topography on the Behavior of Cells," *International Journal of Oral Maxillofacial Implants* 1988; 3:231–246.

(List continued on next page.)

Primary Examiner—Corrine McDermott
Assistant Examiner—Thomas Barrett
(74) Attorney, Agent, or Firm—Connolly Bove Lodge & Hutz LLP

(57) ABSTRACT

An implant element for permanent anchorage in bone tissue in which at least the surface is intended to face the tissue in the implantation region. The element is made of titanium with a titanium oxide surface which has been modified by anodization to acquire oxide thickness of approximately 10–200 nm. Also acquired are an increased surface crystallinity and a roughness on the submicrometer scale in order to provide a high-degree of bone-to-implant contact.

8 Claims, 7 Drawing Sheets

OTHER PUBLICATIONS

B. Chehroudi, et al. "Titanium–coated micromachined grooves of different dimensions affect epithelial and connective–tissue cells differently in vivo," *Journal of Biomedical Materials Research*, vol. 24, 1203–1219, 1990.

C.M. Muller–Mai at al. "Incorporation and Degradation of Hydroxyapatite Implants of Different Surface Roughness and Surface Structure in Bone," *Scanning Microsoft*, vol. 4, No. 3, 1990; pp. 613–624.

D. Buser, et al. "Influence of surface characteristics on bone integration of titanium implants. A histomorphometfric study of miniature pigs," *Journal of Biomedical Materials Research*, vol. 25, 899–902, 1991.

D.C. Smith, et al. "Dental implant materials. I. Some effects of preparative procedures on surface topography," *Journal of Biomedical Materials Research*, vol. 25, 1045–1068, 1991.

C. Larsson et al., "The Ultrastructure of the Interface Zone Between Bone and Surface Modified Titanium",Institute of Anatomy and Cell Biology, Goteborg University, Medicinareg. 3, S–413 90 Goteborg, Sweden, pp. 1–11.

C. Larsson et al., "Bone Response to Surface Modified Titanium Implants", Institute of Anatomy and Cell Biology, Goteborg University, B.–O. Aronsson et al., Department of Applied Physics, Chambers University of Technology, pp. 1–12.

C. Larsson et al., "Bone Response to Surface Modified Titanium Implants" Institute of Anatomy and Cell Biology, University of Goteborg, Medicinareg. 3, S–413 90 Goteborg, pp 1–16.

\* cited by examiner

IMPLANT ELEMENT

This application claims priority to PCT Application No. PCT/SE98/00891, filed May 14, 1998, and Swedish Application No. SE 9701872-5, filed May 16, 1997.

BACKGROUND OF THE INVENTION

Oral implants are made of syntetic materials and inserted in mucosal soft tissues and bone to serve as anchorage for prosthetic constructions. The choice of materials for bone anchorage has been discussed and considered over the years (reviewed in (Brånemark, 1996)) Osseointegrated titanium implants ad modum Brånemark have been successfully used for 30 years. There are several factors which are assumed to play important roles for the outcome of this treatment, for instance the choice of titanium with its adequate mechanical properties and corrosion resistance (Williams, 1981), surface topography and the relatively non-traumatic surgical procedures.

It is assumed that two-stage surgical procedure with an early post-operative period (3–6 months) without loading is important for the initial implant stability during the early healing phase. However, the two-stage surgical technique may be a disadvantage for the patient and requires more resources. In clinical practice, not only the materials and surgical procedures but also systemic and local host factors set the limits for treatment. It has been found that the failure rates are higher in the maxilla and the posterior mandible and that the success rates very much depend on the quality of bone (Esposito et al., 1997). It is therefore of importance to identify the beneficial and negative factors related both to the implant and the host in order to optimize the implant treatment. A reduction of the healing period and a maintenance of long-term stability during clinical loading conditions therefore appears essential.

A biomaterial is a material used in a medical device, intended to interact with biological systems (Black, 1992). The materials used in man-made structures may be divided into three classes: metals, ceramics and polymers. The classes are distinguished by the type of interatomic bonding (Cooke et al., 1996).

Metals consist of a large number of small crystallites. Each crystallite is an aggregate of atoms regularly arranged in a crystalline structure. When molten metals (which are amorphous) solidify small crystals (grains) start to grow. The irregularly arranged crystals eventually meet each other which gives rise to boundaries between the crystals, grain boundaries. The imperfect packing of atoms in the boundaries constitutes weak points in the material, which will be most strongly affected by a surface treatment such as etching or plasma cleaning and a groove will be created showing up as a darker line. The surface properties of a material is different from the bulk properties.

The term commercially pure (CP) titanium is applied to unalloyed titanium and includes several grades containing minor amounts of impurity elements, such as carbon, iron and oxygen. The amount of oxygen can be controlled at different levels to provide increased strength. There are four grades of titanium where grade 1 (used in the present thesis) contains the lowest amount of oxygen. The microstructure of CP titanium is essentially all α titanium which has a HCP crystal structure.

Titanium dioxide, $TiO_2$, is the most common and stable of the titanium oxides, while $Ti_2O_3$ and $TiO$ are more rare (Lausmaa, 1991).

$TiO_2$ can exist in three crystalline modifications; anatase (tetragonal structure), rutile (tetragonal), and brookite (orthotrombic). Rutile and anatase are the most usual forms whereas brookite is very rare (Keesman, 1966).

Techniques have been developed to alter and modify the surface properties of implants via mechanical and chemical procedures (Lausmaa, 1996; Smith et al., 1991a; Smith et al., 1991b). Plasma-spraying, sputter deposition, oxidation, vaporization, (grit, sand) blasting, grinding, etching, plasma cleaning and ion bombardment are examples of techniques available for this purpose.

Electropolishing is an electrochemical technique often used to obtain an improved surface finish by controlled dissolution of the surface layer of the metal. The amorphous surface layer produced by the machining of the implants is removed. After electropolishing a polycrystalline surface with a surface oxide consisting mainly of $TiO_2$, typically 3–5 nm thick as measured by X-ray photoelectron spectroscopy (XPS), is found on the surface (Lausmaa, 1996).

Anodic oxidation is an electrochemical method used to increase the thickness of the oxide layer on metal implants. A current is applied in an electrolytic cell in which the sample is the anode. When a potential is applied on the sample, the current will transport oxygen containing anions through the electrolyte and a continuous oxide is formed on the metal sample. The stoichiometry of anodic oxides on titanium is mostly $TiO_2$. The anodic oxides on titanium contain various structural features such as porosity (Lausmaa, 1996).

In order to characterize the surface properties after the modifications the following techniques were used; SEM and AFM for surface topography and roughness; ESCA and AES for surface composition and oxide thickness.

Interactions Between Titanium Surfaces and Proteins/Cells/Tissues

A review of the literature shows that surface modifications influence the biological response. The first events that take place when an implant is inserted in vivo is the exposure of the material surface to water and biomolecules, including plasma proteins. Both under in vitro and in vivo conditions serum proteins are known to adsorb to foreign material surfaces within seconds. The adsorption and desorption phenomena on different biomaterial surfaces have been studied intensely. A working hypothesis is that the biological response is directed by the initial protein adsorption which subsequently influence the cellular/tissue response and ultimately the performance of the implant (Horbett, 1996).

Three types of adsorption/desorption patterns have been described for metals and their oxides (Williams and Williams, 1988). For example, titanium was found to adsorb low levels of albumin, which remained low during a 48 h period. In addition, the albumin desorbed relatively easily. Other metal surfaces such as vanadium, showed an initially low amount of albumin, but the amount increased and desorption was slow. Gold was found to be characteristic for a surface with a high initial adsorption of albumin and the amount increased throughout the experiment.

A modification and variation on surface properties and the resulting effects on molecular adsorption to surfaces may provide important insights into the role of surface properties for biological reactions. Modified and characterized surfaces have been used to detect differences in the behaviour and adsorption patterns of proteins (McAlarney et al., 1991; McAlarney et al., 1996; Nygren, 1996; Shelton et al., 1988; Sunny and Sharma, 1990; Tengvall et al., 1992; Wälivaara et al., 1994; Wälivaara et al., 1992). Shelton et al (1988) found that a larger amount of proteins were adsorbed to negatively charged polymer beads than to positively charged beads but the roughness of the surface did not seem to influence protein adsorption or cellular behaviour. In general, rough surfaces are considered more wettable than smooth surfaces which may be an effect caused by an increase of the surface area as well as by an increased hydrophilicity of the surface (Curtis et al., 1983).

Nygren (1996) found two different reactions when hydrophilic and hydrophobic titanium surfaces were exposed to whole blood. On the hydrophobic surface, adherent platelets and fibrinogen were present while complement factor 1 (C1) and prothrombin/thrombin were present on the hydrophilic surface. Baier et al. (1982) has reviewed the principles of adhesive phenomena in diverse systems and he pointed out the wettability of a surface as the important parameter influencing the protein adsorption pattern.

The surface energy of a material is influenced by various cleaning procedures and the oxide thickness. According to Sunny and Sharma (1990) an increase of the oxide layer on aluminium, increased the hydrophobicity of the surface, resulting in an increased adsorption of fibrinogen. In addition, the glow discharge technique rendered the surface more hydrophilic causing less fibrinogen adsorption. However, other results were obtained by Wälivaara et al (1994) who found that the titanium oxide thickness and carbon contamination had no influence on protein adsorption and contact activation. Interestingly, increased surface concentrations of complement factor 3 (C3) was correlated with an increasing titanium dioxide film thickness and/or crystallinity. The oxide crystallinity seemed to be of more significance than the oxide thickness (McAlarney et al., 1996). In another study, McAlarney (1991) found that C3 adsorbed preferentially onto grain boundaries which may be explained by the differences in surface energy between grain boundaries and bulk surface. It is known that titanium oxide surfaces bind cations, particulary polyvalent cations (Abe, 1982).

The oxide layer is highly polar and attracts water and water-soluble molecules. In general therefore, calcium ions may be attracted to the oxide surface by electrostatic interaction with oxygen ($O^-$). In a study by Lausmaa et al (1988), approximately 100 samples prepared according to clinical procedures were analyzed with ESCA. The spectra showed that the surface consisted mainly of $TiO_2$. Carbon and smaller amounts of N, Cl, Ca, S, P, Na and Si were found on the surface but after sputtering all were removed except for Ca which was found throughout the oxide.

It is of a major interest to understand, on a time-scale from immediate responses to years, how material properties influence cellular activity in the interface and vice versa since rejection, excessive scar formation/encapsulation by fibrous tissue and restitution of original tissue may largely influence the performance of the implant. In soft tissues a fibrous capsule is formed around the implant (phenomenon of walling off the material from the biological environment) (Thomsen and Ericson, 1991). In bone, encapsulation of the implant by fibrous tissue may occur but is not obligatory and instead mineralized bone can establish direct contact with the implant, a process called osseointegration (Brånemark et al., 1969). Although the work on cell-material interactions has been intensified during recent years, the mechanisms by which material properties influence biological reactions are still not clear. Studies in vitro.

The attachment of tissues to implants in vivo is a complex matter because in most cases there are different types of tissues involved which may behave differently at different surfaces. The response of cells to variations in culture substrate topography varies for different cell types like macrophages (Rich and Harris, 1981; Salthouse, 1984), fibroblasts (van der Valk et al., 1983), periodontal cells (Cochran et al., 1994), epithelial cells (Chehroudi et al., 1989; Chehroudi et al., 1990), osteoblasts (Bowers et al., 1992; Martin et al., 1995) and chondrocytes (Schwartz et al., 1996).

Rich and Harris (1981) showed that macrophages accumulated preferentially on less hydrophilic as well as on roughened substrata. Murray et al (1989) showed that when macrophages adhered to hydrophilic surfaces $PGE_2$ release and bone resorption was stimulated compared with hydrophobic surfaces. In addition, the rough surfaces was found to stimulate bone resorption to a greater extent than smooth surfaces. Although the roughness and the surface energy of the different surfaces were not quantitated this indicates that the interactions between macrophages and implant surfaces cause a release of factors which is higher than if cells are in suspension. Studies on human monocyte interactions with titanium surfaces have shown that the interleukin-1 release by the cells is modulated by protein adsorption and the presence of material particles (Gretzer et al., 1996).

Interestingly, different results have been obtained with fibroblasts. Human fibroblasts attached better to smooth than to rough titanium surfaces, (polished with 1 $\mu$m diamond paste versus the rougher; prepared with 240 or 600 grit silicon carbide metallographic papers) (Keller et al., 1989). Spreading of fibroblasts was found to depend on the polar surface free energy (van der Valk et al., 1983) since at least on various polymer surfaces, low cell spreading was found on low polar parts. Sukenik et al (1990) modified titanium surfaces with different covalently attached self-assembled monolayers (four different chemical endgroups; $CH_3$; C=C; Br; Diol). The neuroblastoma cell attachment to the different surfaces was comparable but cell spreading was least pronounced on the most hydrophobic surface ($CH_3$ and C=C)

Osteoblasts are sensitive to subtle differences in surface roughness and surface chemistry and respond to altered surface chemistry by altering proliferation, extracellular matrix synthesis, and differentiation (Boyan et al., 1995). Osteoblasts exhibited different phenotypes when cultured on rutile or amorphous $TiO_2$ surfaces, but with the same oxide thickness and degree of roughness. Differences were therefore suggested to be attributed to crystallinity alone (Boyan et al., 1995).

Osteoblasts have an initial greater attachment to rough, sandblasted titanium surfaces with irregular morphology but average roughness ($R_a$) parameters did not predict cell attachment and spreading in vitro (Bowers et al., 1992).

Proliferation and differentiation parameters in osteoblast-like cells were modified by growing cells on titanium discs with an increased roughness (15–18 $\mu$m) (Martin et al., 1995). Interestingly, cells at different stages of differentiation responded differently to the same surface (Boyan et al., 1995; Schwartz et al., 1996).

A basis for most studies in vitro on the role of surface properties for cell function is the adhesion of cells to the surface of the culture dish. The resulting interactions between the cell and the surface, with or without adsorbed molecules, is therefore a fundamental and obvious part of the experimental set-up. In this context it may also be argued that the properties of the material surface as stimulating or inhibiting factors on cells could be over-emphasized in relation to other potential and maybe equally important modulating factors present in the vicinity of cells and surfaces in the complex biological situation in vivo.

Studies on titanium implants in bone (Sennerby et al., 1993a; Sennerby et al., 1993b), indicated that osteoblasts did not adhere to the implant surface and that formation of bone was not initiated at the surface. This observation suggests that the studies on the interaction between osteoblasts and titanium surfaces in vitro is of minor relevance. Nevertheless, studies in vitro, where various aspects of the complex in vivo situation can be studied in detail may be of great value but this requires that the conditions in vivo are considered when the in vitro system is designed.

On the basis of the published in vitro studies it may be concluded that the surface roughness appears to influence the cell proliferation albeit differently depending on the degree of cell maturation. Differences in surface properties may influence the cell attachment and proliferation although the mechanism is not clear. It is also evident that different cell types are differently influenced by the surface properties. However, so far there are few studies on the effect of modified titanium surfaces on cellular behaviour. A review of the literature on the in vivo response to titanium implants is therefore appropriate.

In general, histology, histochemistry and immunohistochemical techniques have been used for the evaluation of soft tissue reactions. Due to technical difficulties to obtain thin sections of an intact metal-tissue interface the ultrastructure of the interface tissue has been difficult to study (Ericson and Thomsen, 1995). However, for metals in soft tissues, an electropolishing method by which the bulk metal, but not the thin surface oxide layer, is removed (Bjursten, 1990) have made such studies possible.

The macrophage plays a pivotal role during healing of soft tissue around implants. The soft tissue response to titanium implants in rats is described by Thomsen and Ericson in (Bränemark et al., 1995). A fluid space, containing cells and proteins was present during the early phase (1–2 weeks) after introduction of a titanium implant in soft tissues (Johansson et al., 1992; Röstlund et al., 1990). The concentration of leukocytes and the proportion of PMN in the fluid space decreased between 1 and 7 d (Eriksson et al., 1994). After one week the majority of inflammatory cells in the fluid space, predominantly monocytes and macrophages, were attached to the fibrin matrix at the border between the fluid space and the reorganized tissue rather than to the implant surface. After six weeks the fluid space was largely absent and the macrophages had established contact with the implant surface (Johansson et al., 1992; Röstlund et al., 1990). Macrophages constituted the most common cell type at the titanium surface, and exhibited different phenotypes, as judged by their ultrastructure (Johansson et al., 1992). Immunohistochemical observations (Rosengren et al., 1993) show that the fluid space around a titanium implant one week after implantation contained albumin, complement factor C3c, immunoglobulins, fibrinogen and fibronectin. Albumin and C3c were distributed in the fluid space and throughout the tissue interstitium during the first week. Fibrinogen and fibronectin co-localized preferentially at the border between the fluid space and the tissue, thus forming a provisional matrix to which macrophages and fibroblasts adhered.

After 6 and 12 weeks, fibrinogen was not detected in the surrounding tissue whereas strands of fibronectin was found in the surrounding capsule (Rosengren et al., 1996). Collagen type I immunoreactivity, coinciding with the collagen bundles in the surrounding tissue, had a distribution similar to that of fibronectin, reaching close to the titanium surface, but always separated from it by one to several layers of macrophages after 12 weeks.

The general sequence of cellular migration and accumulation as well as the leakage of plasma into the tissue in the immediate vicinity of the implant surface has been observed after implantation of several different materials, including metals, in soft tissues (Thomsen and Ericson, 1991). The tissue response around nitrogen-ion implanted titanium discs inserted in the rat abdominal wall of rats was not significantly different from that observed around pure titanium implants. However, after 6 weeks a predominance of macrophages and multinuclear giant cells was found around the nitrogen-ion implanted discs (Röstlund, et al., 1990). A comparison of titanium and Ti6Al4V after 1, 6 and 12 weeks in the same rat abdominal wall model did not reveal any differences with regard to cell types and numbers in the interface (Johansson et al., 1992). Further, the authors did not find any difference in fibrous capsule width. Therin et al. (1991) showed similar results when comparing the capsule thickness for titanium, $TiO_2$-coated titanium, Ti6Al4V, $TiO_2$-coated Ti6Al4V, TiN-coated Ti6Al4V, Ti5Al2.5Fe and stainless steel (316 L).

In contrast to polymers (Chehroudi et al., 1989; Chehroudi et al., 1990) studies in soft tissues which have been focused on the biological effects of altered surface topography and roughness of metal implants are relatively few.

However, in an extensive light microscopical study on the effects of surface roughness variations of titanium and stainless steel, (Ungersböck et al., 1994) it was shown that smooth implants induced a thicker soft tissue capsule with an intervening fluid space. In contrast, blasted and anodized titanium plates with relatively high values of roughness parameters (Ra 0.75) were surrounded by a significantly thinner soft tissue layer without a continuous liquid space. On the basis of these results it is difficult to conclude that there exists a simple relationship between increased surface roughness and capsule thickness. For instance, $Al_2O_3$-blasted titanium plates with an even greater surface roughness ($R_a$ 1.5) had a capsule thickness which was similar to that around blasted, anodized titanium samples. Further, tumbled titanium plates ($R_a$ 0.15) had a capsule thickness which was similar to tumbled and anodized smooth titanium ($R_a$ 0.33). The roughness was measured with a profilometer and the elemental composition of implant surfaces was not reported. It is therefore possible that the surface chemical composition and/or roughness on the submicrometer level, differed between the samples. Studies on the effects of various surface topographies (smooth vs. various microtextures between 1 and 10 $\mu$m) of titanium discs implanted in soft tissues of rabbits showed that collagen type III immunoreactivity was detected in the fibrous capsule around several materials, but that collagen type I was positively stained only in capsules around titanium (von Recum et al., 1993).

In general, the experimental studies in soft tissues indicate that metals become surrounded by a fibrous capsule with macrophages located closest to the surface, thus separating fibroblasts from the surface. So far there are few available morphological data on the interface structure around titanium surface modifications. It is still an open question how the material surface properties influence protein adsorption during in vivo conditions and how the surface properties influence the cells close to the surface. Moreover, it is not understood how the composition and structure of the surrounding fibrous capsule is influenced by the material surface-macrophage interactions. It is likely that several additional factors must be considered, including leaching of metal ions, loading conditions and micromovements between the implant surface and tissue.

The response of bone to injury is regeneration followed by remodelling of the newly formed bone in the direction of stresses. Analogously, when an implant is inserted in bone, a similar cascade of events is expected to occur including the recruitment of mesenchymal cells to the wound site, their differentiation into osteoblasts, synthesis of osteoid, and calcification of the extracellular matrix. The mesenchymal progenitor cells are pluripotent and able to differentiate into osteoblasts, chondrocytes, muscle cells and fat cells (Caplan and Boyan, 1994). The pathway of differentiation of the mesenchymal cells as well as regeneration of bone around an implant is most likely dependent on a combination of factors including the degree of trauma, local and systemic factors as well as implant properties and stability.

In the following a short summary of previous work on the interaction between metal implants and bone will be given. The performance of non-metal implants is reviewed elsewhere (de Groot et al., 1994).

Studies comparing the performance of, different implants of metals including Vitallium®, niobium, titanium, titanium alloy, stainless steel (Johansson et al., 1991), and zirconium (Albrektsson et al., 1985; Johansson et al., 1994) in bone, did not reveal any major qualitative differences. The threaded titanium implants were in general found to be in contact with more mineralized bone than the other types of metal. The mechanisms for this is not clear nor is it understood why the properties of titanium are advantageous for biological applications compared with other metals, including those nearby in the periodic system. The good biological performance of titanium has been attributed to the titanium oxide layer covering the surface, but no compelling evidence for this view has been presented.

Several studies have indicated that an increased roughness of implant surfaces (within a certain range) enhance the biomechanical performance of implants. However, the bone response seldom show differences although some studies indicate an increased bone-implant contact with increased surface roughness (Buser et al., 1991; Goldberg et al., 1995; Gotfredsen et al., 1995). Most studies did not reveal such a correlation (Carlsson et al., 1988; Gotfredsen et al., 1992; Thomas and Cook, 1985; Thomas et al., 1985; Thomas et al., 1987; Wennerberg 1996; Wilke et al., 1990; Wong et al., 1995). Branemark (1996) made a correlation between morphological parameters of osseointegration of threaded titanium implants and different biomechanical tests and found that pull-out tests mainly reflects the mechanics of the surrounding bone while removal torque tests reflects the shearing forces leading to plastic deformation of the bone-implant interface. Possibly biomechanical tests performed on implants with a rough surface (micrometer level), inserted in bone mainly reflect the bone-material mechanical interaction (interlocking) although it cannot be excluded that differences in the structure of the interface not resolved by light microscopy are of importance.

Using an animal model similar to that used in the present study Sennerby et al (1993b), studied the bone response 3–180 days after insertion of screw-shaped titanium implants. At 3 days mesenchymal cells were migrating into the injury area around the implants. The implant surface was temporarily covered by multinuclear giant cells which disappeared with time and when bone-titanium contact increased. Newly formed bone extended from the endosteal surface towards the implant and was also formed as islands within the implant threads.

With time the two types of newly formed bone fused. The threads originally protruding into the marrow cavity were gradually filled with bone which matured by remodelling. Formation of new bone directly at the titanium surface was not observed at any time interval.

Only a limited number of studies of the ultrastructure of the bone-metal interface tissue are available. This may reflect the fact that the preparation of the interface tissue for analysis by transmission electron microscopy TEM is technically demanding, especially when the decalcification step is omitted.

Albrektsson et al (1982) introduced polycarbonate plugs coated with a thin layer of evaporated metal as a model for metal implants. The plugs were implanted in the rabbit tibia. TEM on partially decalcified specimens showed the presence (after 3 months) of collagen bundles close to titanium implant but the last 100–500 nm closest to the implant consisted of randomly arranged filaments. A 20–40 nm thick layer of partially calcified amorphous substance, suggested to consist of proteoglycans was found in contact with the implant surface. A gradient of decreasing mineralization towards the implant surface was also described. In contrast, a larger number of macrophages and osteocytes were found at gold-coated plugs. In more recent studies based on the plastic plug technique, other metal coatings including zirconium has been compared with titanium (Albrektsson and Hansson 1986; Albrektsson et al., 1985).

Linder et al (1989), studied the interface morphology of plugs of titanium. Ultrastructural observations in rabbit cortical bone (11 months observation period) adjacent to titanium, Tivanium®, Vitallium®, and stainless steel revealed an unpredictable variation in interface ultrastructure within 500–1000 nm of all metal surfaces. Three main types of interface structure were found; a) More or less regularly arranged fibrils of collagen, with the longitudinal cross-banding of 68 nm typical of type-I collagen, approaching the metal surface to within 50 nm: b) Type-I collagen fibrils separated from the implant by a zone of indistinct structures, but with some filamentous material, most often about 500 nm in thickness, but sometimes up to 1000 nm; c) Type-I collagen fibrils separated from the implant by a 500–600 nm zone of thin filamentous structures, clearly more dense than in b. There was no structural feature that was specific for a particular material (Linder et al., 1989).

Sennerby et al (1992) examined the interface morphology of titanium implants inserted into the rabbit tibia for 12 months and found mineralized bone to be present very close to the implant surface without any apparent decreasing gradient of the concentration of bone mineral towards the implant surface. A thin layer of amorphous non-mineralized material (100–200 nm wide) was present peripheral to the mineralized bone. In addition, visible when mineralization was low, an about 100 nm wide electron dense lamina limitans was found to form the border between mineralized bone and the amorphous layer. This lamina limitans were often seen in direct continuity with lamina limitans bordering osteocyte canaliculi or separating bone of different mineralization grades.

Steflik studied the interface morphology at various types of implants in the dog mandible using TEM and high voltage TEM and found an about 50 nm wide electron dense deposit at the implant surface (Steflik et al., 1992a; Steflik et al., 1992b). No difference was seen between loaded and unloaded implants (Steflik et al., 1993).Nanci et al (1994) studied the tissue response to titanium implants inserted for 1 day to 5 months in tibia and femur of rats. The morphology of the interface tissue varied. Most often the interface between bone and the titanium implant consisted of a thin, electron-dense layer. This interfacial layer was found both adjacent to mineralized bone and unmineralized collagen. With immunocytochemical techniques, the electron-dense layer described as lamina limitans was shown to be immunoreactive for osteopontin. The cement lines in the surrounding bone often in continuity with the lamina limitans at the implant surface, showed a similar immunoreactivity for osteopontin. Osteocalcin, fibronectin, and albumin showed no preferential accumulation at the interface. In a recent study McKee and Nanci, (1996) are suggesting that osteopontin functions as a mediator of cell-matrix and matrix-matrix/mineral adhesion during the formation, turnover and repair of mineralized tissue. A review of the literature on the soft tissue response to titanium implants is important since a penetration through skin and mucous membranes is necessary to allow the attachment of external prosthetic appliances (e.g. teeth and epistheses). Interest has been focused on the prerequisites for an adequate adaptation of the soft tissue to the penetrating element. Empirically it has been found that a careful surgical technique with minimal motion at the interface by a tight adherence of the soft tissues to the underlying bone may provide adequate conditions for clinical percutaneous and permucosal implants/anchorage units.

In studies on the relationship between the titanium surface and epithelium and connective tissues the majority of observations in humans have been made in specimens from the oral cavity (Sanz et al., 1991; Seymour et al., 1989; Tonetti et al., 1993) and from the craniofacial region (bone conductive hearing aids) reviewed in (Holgers 1994). In a light microscopic and ultrastructural study of oral implants (Sanz et al., 1991) the inflammatory infiltrates were scarce in the non-infected peri-implant tissue. However, when gingivitis was observed, the inflammatory infiltrates were larger, dominated by mononuclear cells and plasma cells. (Seymour et al., 1989) characterized the mucosa around Brånemark osseointegrated titanium implants. The samples were obtained from healthy mucosa or with clinical signs of inflammation (gingivitis). The authors reported the presence of inflammation in both situations (healthy gingiva or gingivitis) but found larger inflammatory infiltrates and higher cell numbers when clinical signs of gingivitis were present. The authors concluded that the mucosal reaction was a stable and well controlled response. Similar findings were reported around clinically functioning bone-anchored percutaneous implants (Holgers, 1994), suggesting that an immunological compensation for the loss of barrier function is present at implants with clinically irritated skin. The relationship between epithelial cells and the surface of implants as well as the common observations of epithelial downgrowth have been suggested to play an important role for the function of implants, both in oral and percutaneous applications. In contrast to observations for dental implants (Listgarten and Lai, 1975; Schroeder et al., 1981), no close contact between the epithelium/collagenous tissue and the surface of percutaneous titanium implants were seen (Holgers et al., 1995).

In conclusion, these observations indicate that machined titanium implants in soft tissues of humans are surrounded by inflammatory cells which appear to provide a protective barrier which may compensate for a non-optimal epithelial barrier.

Analysis of a retrieved osseointegrated clinical titanium implant (3 months) (Lausmaa J. 1988) revealed an increased oxide thickness (by factor 2–3) compared with an unimplanted sample. Similar in vivo oxide growth have been reported earlier. By the use of Auger electron spectroscopy, McQueen et al. (1982) observed that after 6 years in human jaw bone, the original 50 Å thick oxide layer on titanium implant surfaces had increased to a 2000 Å thick oxide layer.

Sundgren et al (1986) investigated the interface of bone-titanium and bone-stainless steel in humans and found that both the thickness and the nature of the oxide layers on the implant had changed during the time of implantation. Depending on the location, the thickness remained unaffected (cortical bone) or increased with 3–4 times (bone marrow). In both cases, Ca and P were incorporated in the oxides. For titanium implants the oxidation process occurred over a longer time period (several years).

In a light microscopical study by Sennerby et al. (1991), seven clinically stable (1–16 years) osseointegrated dental implants, were analyzed morphometrically. The major part of the implants were in contact with mineralized bone (56–85%), irrespective of observation period. Carlsson et al (1994) evaluated the tissue around implants with different roughness inserted experimentally in arthritic knees. Blasted titanium and hydroxyapatite-coated implants were in contact with bone whereas smooth titanium implants often were surrounded by fibrous tissue .

Sennerby et al (1991), examined the structure of the interface around seven clinically stable dental implants (1–16 years) by morphometry. In areas with mineralized bone close to the titanium surface, a non-mineralized amorphous layer was observed. An electron dense lamina limitans-like line was observed between the mineralized bone and the 100–400 nm wide amorphous zone.

Ultrastructural observations were made on the metal-bone of interface of implants inserted in the tibia of patients with arthrosis and rheumatoid arthritis (7–20 months) (Serre et al., 1994) The implants were all screw-shaped pure titanium implants and they were all "osseointegrated". No difference between the ultrastructure of the interface between normal bone and implants compared with the interface of arthrotic and arthritic bone was observed. The heterogeneity of the interface was also confirmed in this study although the 100–400 nm wide amorphous zone reported by Sennerby et al (1991), was not found.

In an ultrastructural study of the interface of a plasma-sprayed titanium dental implant inserted in man (ITI), (Hemmerlé and Voegel, 1996), two different interfacial structures were noticed. Both bone crystals directly apposed on the implant surface and a granular electron-dense substance interposed between the plasma-sprayed coating and the bone were observed. Rohrer et al (1995) examined non-decalcified histologic sections from 12 osseointegrated titanium plasma spray-coated (TPS) and TPS-treated with hydroxyapatite implants (IMTEC) from one patient. All implants were successful and stable after 1 year when the samples were retrieved. Both implant types were used with the same success and no morphological differences were observed between the two implant types.

BRIEF DESCRIPTION OF THE DRAWINGS

This invention will be better understood by reference to the Detailed Description of the Invention when taken together with the attached drawings, wherein.

Figure 1:
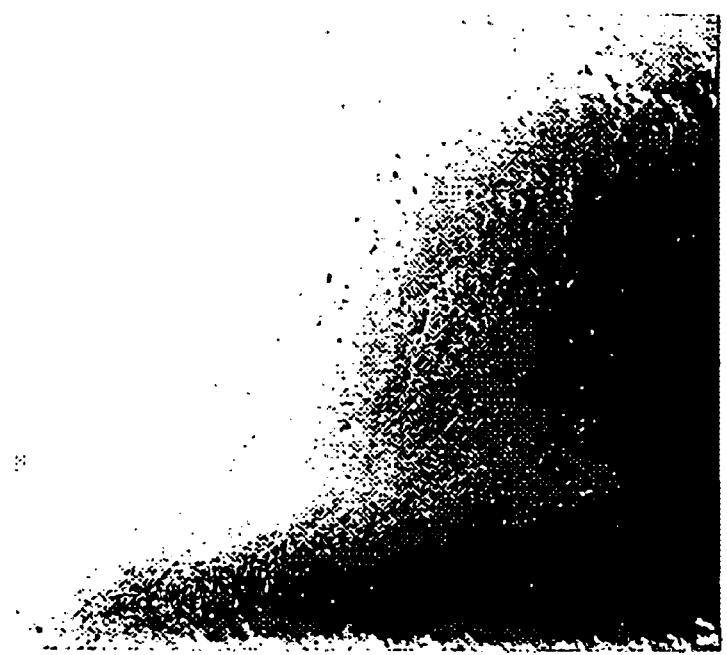
FIGS. 1a to 1c is a scanning electron micrograph (SEM) representing an electropolished and anodized implant.
FIG. 1d is a SEM representing a machined and anodized implant.
Figure 1:
Figure 1:
Figure 1:
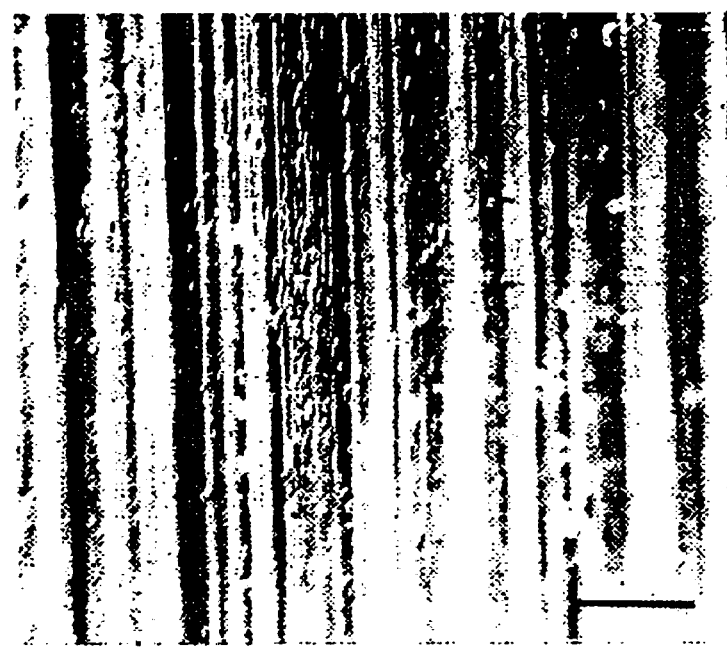

The following invention is based on a comprehensive experimental study using differently modified titanium surfaces. In the following the experimental procedures are summarized. Details may be found in a thesis, (C. Larsson: The Interface between bone and metals with different surface properties) including the following papers;

I. C. Larsson, P. Thomsen, J. Lausmaa, M. Rodahl, B. Kasemo and L. E. Ericson. Bone response to surface modified titanium implants. Studies on electropolished implants with different oxide thicknesses and morphology. Biomaterials 1994 (15) 13, 1062–1074

II. C. Larsson, P. Thomsen, B-O Aronsson, M. Rodahl, J. Lausmaa, B. Kasemo and L. E. Ericson. Bone response to surface modified titanium implants. Studies on the early tissue response to machined and electropolished implants with different oxide thicknesses. Biomaterials 1996 (17) 6, 605–616

III. C. Larsson, P. Thomsen and L. E. Ericson. The ultrastructure of the interface zone between bone and surface modified titanium. (In manuscript)

IV. C. Larsson, P. Thomsen, B-O Aronsson, M. Rodahl, J. Lausmaa, B. Kasemo and L. E. Ericson. Bone response to surface modified titanium implants. Studies on the tissue response after one year to machined and electropolished implants with different oxide thicknesses. Journal of Materials Science: Materials in Medicine, submitted V. C. Larsson, P. Thomsen, J. Lausmaa, P. Tengvall, B. Wälivaara, M. Rodahl, B. Kasemo and L. E. Ericson. Bone response to surface modified titanium implants. Studies on the early tissue response to different surface characteristics. (In manuscript)

Threaded screw-shaped implants were manufactured by machining of: pure titanium (grade I, 99.7%) (Permascand, Ljungaverk, Sweden)

The implant surfaces were modified with different preparation techniques (summarized in table I). Details of the different surface modifications are found in the separate papers (I–V). All implants had a length of 4 mm and a diameter of 3.75 mm.

Circular, disc-shaped implants (ø 10 mm, thickness 1.8 mm), were manufactured by machining of a titanium rod (99.7%) (Permascand, Ljungaverk, Sweden). These implants were used for studies on protein adsorption in vitro and inflammation in soft tissues.

The techniques for preparation and surface modification of the three types of implants (machined, electropolished, and electropolished plus anodized) used in the additional experiments a) and b), are described in detail in paper I and II.

During the electropolishing technique the sample is used as an anode in an electrochemical cell. By varying the electrolyte composition and process parameters (temperature, voltage and current) in the cell, various surface treatments can be carried out, including electrochemical polishing (electropolishing) or anodic oxidation (anodization).

The electropolishing technique which acts as a controlled electrochemical dissolution of the surface (Landolt, 1987), was carried out at 22.5 V in an electrolyte consisting of a mixture of 540–600 ml methanol, 350 ml butanol and 60 ml perchloric acid held at −30° C. Each sample was polished for 5 min. which is estimated to remove less than 100 $\mu$m of material from surface. The electropolishing procedure was carried out in order to produce a smooth, mirror-like surface finish. It also has the effect of removing the plastically deformed amorphous surface layer which results from machining of the material. After electropolishing, the samples were carefully rinsed in methanol in order to remove electrolyte residues.

Anodic oxidation (anodization) (Ross, 1975) was carried out at 80 V in a M acetic acid electrolyte at room temperature. This procedure produced a vivid, greyish-purple colouration of the surface, due to light interference in the thick oxide that was formed. It is well established that the oxide thickness is linearly dependent on the applied voltage, with a growth constant. α Å 2–3 nm/V for titanium, depending on experimental conditions. The anodized samples were carefully rinsed in deionized water followed by a rinse in ethanol.

Scanning Auger electron spectroscopy (AES; Perkin-Elmer PHI 660, Eden Prairie, USA) was used to analyze the surface elemental composition. Oxide thickness was estimated from AES depth profile analysis. At least 2 different spots (ø 100 $\mu$m), located at the threaded part of the sample were analyzed. Depth profiles were obtained at 2 points (ø 10 $\mu$m).

AES survey spectra were acquired from two areas of ø 200 $\mu$m on one sample of disc-shaped machined, electropolished and electropolished plus anodized titanium implants.

Scanning electron microscopy (SEM; JEOL JSM-T-300, and Zeiss DSM 982 Gemini) was used to obtain an overall picture of the surface topography. Atomic force microscopy (AFM; Nanoscope III, Digital Instruments, USA) was used for a more detailed characterization of the surface topography and roughness. The surface roughness ($R_{rms}$) and surface area enlargement ($A_{diff}$) were calculated using the computer software of the AFM instrument.

Contact angles were measured using a Ramé-Hart goniometer, model 100. Advancing and receding contact angles were determined for titanium (control), electropolished and electropolished plus anodized samples, both with Millipore filtered water and with methylene iodide. One drop (5 $\mu$l) of the liquid, was placed on three different spots on each sample. Both right and left angles of the drop were estimated and the mean values calculated. The samples were cleaned (in addition to the conventional cleaning steps with trichlorethylene, acetone, and ethanol) with 95% ethanol and air-dried within 30 min prior to analysis. Surface energy was calculated and preferred values of surface tension for the liquids in room temperature (Wu, 1982) were used for water and methylene iodide.

The implants were ultrasonically cleaned in trichlorethylene; acetone; methanol. After surface modification (electropolishing and/or anodic oxidation), all implants received a final ultrasonic cleaning step in ethanol (70%). Finally, implants were either autoclaved in 120° C. for 15 min. or γ-irradiated at 28.9 kGy for 25 h at 30° C. The hydrogen peroxide treated implants were treated with 10 mM $H_2O_2$ for 40 h at 8° C. after the ultrasonically cleaning procedure. No additional sterilization was performed.

The disc-shaped implants were ultrasonically cleaned in trichlorethylene; acetone; ethanol. After surface modification (electropolishing and/or anodic oxidation), all implants received a final ultrasonic cleaning step in ethanol.

Rat plasma was obtained from two rats and used in protein adsorption experiments.

Fifteen Sprague-Dawley rats, weighing about 250 g, were used for studies on cell recruitment and adhesion to titanium surfaces in soft tissues.

The surgery was performed according to procedures described earlier, (paper I–V) and implantation was made bilaterally in the proximal tibial bones. After incision through the skin and periosteum, a flap was raised to expose the bone area. Thus, each animal received one implant of each type, respectively.

After the animals were killed, the implants and surrounding tissue were removed en bloc, further immersed in glutaraldehyde over night and then postfixed in 1% osmium tetroxide, for two hours. After dehydration the undecalcified specimens were embedded in LR White® (The London Resin Co Ltd, Hampshire, England).

In studies on protein adsorption in vitro surface adsorbed proteins were collected, separated (SDS-PAGE) and visualized (Western blot). In brief, discs were kept in 99.5% ethanol, ultrasonicated in 99.5% ethanol, washed three times and kept in 99.5% ethanol until use. Before incubation with proteins, the samples were placed in sterile-filtered HBSS with calcium. Rat plasma was incubated on three surfaces of each kind (machined, electropolished and electropolished plus anodically oxidized titanium) during 1 min. at 37° C. Thereafter loosely attached proteins were rinsed off and the surface adsorbed proteins removed by the detergent SDS (2%) together with enzyme inhibitory agents. The total amount of collected proteins was analyzed with BCA Protein Assay Reagent (Pierce, USA) using spectrophotometry (562 nm) and with rat albumin as standard. Gel electrophoresis with precasted Tris-glycine (4–15%) gradient acryl amide gels (BioRad, Miniprotean II) was performed to separate the proteins. After separation the proteins were transferred to nitrocellulose membranes (70 V, 3 h, Tris-glycine-SDS buffer) followed by blocking of unspecific antibody binding by incubation in 3% gelatin in Tris-NaCl buffer, pH 7.5. To detect specific proteins on the membrane 3 incubation steps were performed (60 min., room temp.) in Tris-NaCl-Tween buffer.

The primary step included rabbit anti-rat fibronectin (FN); goat anti-rat fibrinogen (fractions) (FBN); sheep-anti-rat albumin (Alb); sheep anti-rat immunoglobulin G (IgG). The secondary step included biotinylated donkey anti-sheep IgG; biotinylated goat anti-rabbit IgG and the tertiary step included streptavidin conjugated to alkaline phosphatase in Tris-NaCl-Tween (TTBS) buffer. Visualization of the labelled proteins (samples and standard) was made by incubation in BCIP/NBT.

The implantation of implants in soft tissues was performed according to previously described procedures (Lindblad M. et al., 1997). In brief, 15 Sprague-Dawley rats, weighing about 250 g, were anesthetized with an i.p injection (0.1 ml/100 g b.wt.) of a 1:1:2 solution of sodium pentobarbital (Apoteksbolaget, Sweden; 60 mg/ml), 0.9% saline and diazepam (Apozepam®, Apothekarnes Laboratorium AS, Norway; 5 mg/ml). The rats were shaved on the dorsum and cleaned with 2% Jodopax® in ethanol. Incisions, about 15 mm long and 10 mm apart were made in the dorsal skin along the midline. Subcutaneous pockets were created by blunt dissection and implant discs were placed in the pockets using a pair of titanium tweezers. In six rats three incisions were made along each side of the midline. These rats received two of each type of implant: one of these two implants was rinsed in sterile HBSS buffer (Hanks balanced salt solution with $CaCl_2$ 2.9 g/l, pH 7.4) whereas the other implant was rinsed in sterile saline. The other nine each received three implants, one of each type, which were rinsed in saline prior to insertion. The skin was closed with non-resorbable sutures. After 1 (n=6), 3 (n=6) and 7 (n=3) days the dorsal skin of anaesthetized rats was cleaned and the rats killed by an i.p. overdose of pentobarbital. The sutures were taken away and the wound surfaces were gently drawn apart with tweezers. The implants were removed and placed in a sterile polystyrene tissue culture dishes, containing 500 μl sterile HBSS (with calcium) and kept on ice. The remaining content (exudate) of the cavity was collected by rinsing, using repeated aspirations (5 times) of 500 μl (total volume) sterile HBSS (with calcium).

Each retrieved exudate was kept on ice until the determination of cell count and cell types. The exudates were stained with Turk solution and the proportion of different cell types was determined. The total mean of the number of cells found in the exudate was calculated from six (1 and 3 d) and three (7 d) rats per time period and the percentage mean values of different cell types were calculated in the same way.

The determination of the amount of DNA associated with the implant surfaces was performed with a fluorescence assay (Labarca C. and Paigen K. 1980). In brief, after the retrieval procedure each implant was put in 500 μl $5 \times 10^{-2}$ M sodium phosphate buffer with $2 \times 10^{-3}$ M EDTA and 2 M NaCl. Thereafter, the implants were frozen at −20° C. After thawing and ultrasonication of the cells on the implants (about 15 s at each side of the implant), 200 μl of the solution was added to $5 \times 10^{-2}$ M sodium phosphate buffer with 2 M NaCl, supplemented with 1 μg $ml^{-1}$ of the fluorescence marker Hoechst 33258 (Sigma, USA) at room temperature (15–30 min.). The samples were measured in a luminescence spectrometer with excitation and emission wavelengths of 360 and 450 nm, respectively. The total amount of DNA was determined from standard curves (0.025–2.5 μg DNA per ml). The total mean of the DNA amount associated with the implant surfaces was calculated from six (1 and 3 d) and three (7 d) rats per time period.

Ground sections of 10–15 μm thickness were prepared from implant/bone specimens (Donath and Breuner, 1982), and examined, using a Leitz Microvid equipment connected to a personal computer. Measurements were performed directly in the microscope. The contact ratio between the implant surface and bone tissue was calculated. Similarly, the proportion of bone tissue within the threads along the implant was calculated. The data are given as percentage bone in direct contact with the implant (referred to as bone contact) and percentage of the total area within the threads occupied by mineralized bone (referred to as bone area). All five consecutive threads (with number 1 and 2 located in the cortex) were evaluated. In the one-year study, the values for the 3 best consecutive threads were also presented. The mean value for each implant type at each time period was calculated and compared. After polymerization embedded implants were divided longitudinally by sawing. One half was used to prepare ground sections (Donath and Breuner, 1982) which were used for morphometric analysis (papers I–II, IV–V) as described above. The other half was used for the preparation of sections for light and electron microscopy (papers I, IV). The implant was carefully separated from the plastic embedded tissue (Sennerby et al., 1992; Thomsen and Ericson, 1985). The cavity formed after implant removal was filled with plastic resin and polymerized before sections for LM (approximately 1 μm thick) were cut with glass knives. In these sections appropriate areas were selected for ultramicrotomy. Ultrathin sections, contrasted with uranyl acetate and lead citrate were examined in Philips EM 400 or Zeiss CEM 902 electron microscopes.

Results

A summary of the results from surface characterization of the different samples (papers I–V) is presented in Table I.

Machined (control), electropolished, electropolished plus anodized (21 nm thick oxide) and electropolished plus anodized (180 nm thick oxide) were used in paper I and III. The machined titanium implants (control) had typical machining grooves in the width of 1–10 $\mu$m. The electropolished implants had a very smooth, mirror-like surface with no apparent surface features at low or high magnification. The anodized (21 nm) samples also appeared smooth whereas the anodized (180 nm) had porous regions irregularly distributed over the smooth surface which made the implant surface roughness heterogeneous (1 $\mu$m scale). $R_{rms}$ values obtained by AFM are presented in Table I.

Machined (control), machined plus anodized (180 nm thick oxide) electropolished, and electropolished plus anodized (180 nm thick oxide) were used in paper I and III.

Figure 2:
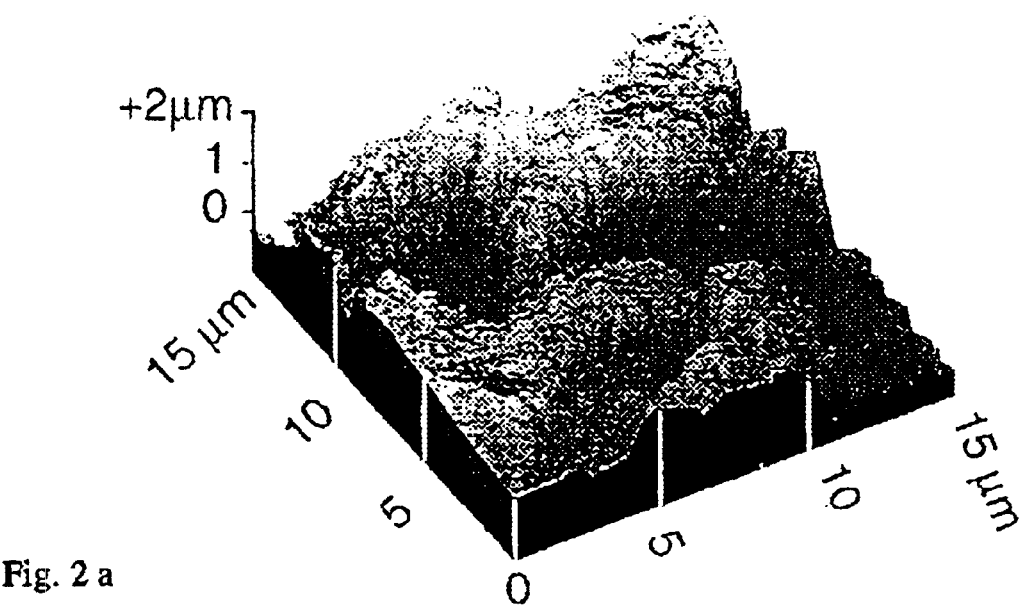
FIG. 2a is an atomic force micrograph (AFM) representation of a rough part of an electropolished and anodized implant.
FIG. 2b is an AFM representation of a smooth part of an electropolished and anodized implant.
FIG. 2c is an AFM representation of a machined and anodized implant.
Figure 2:
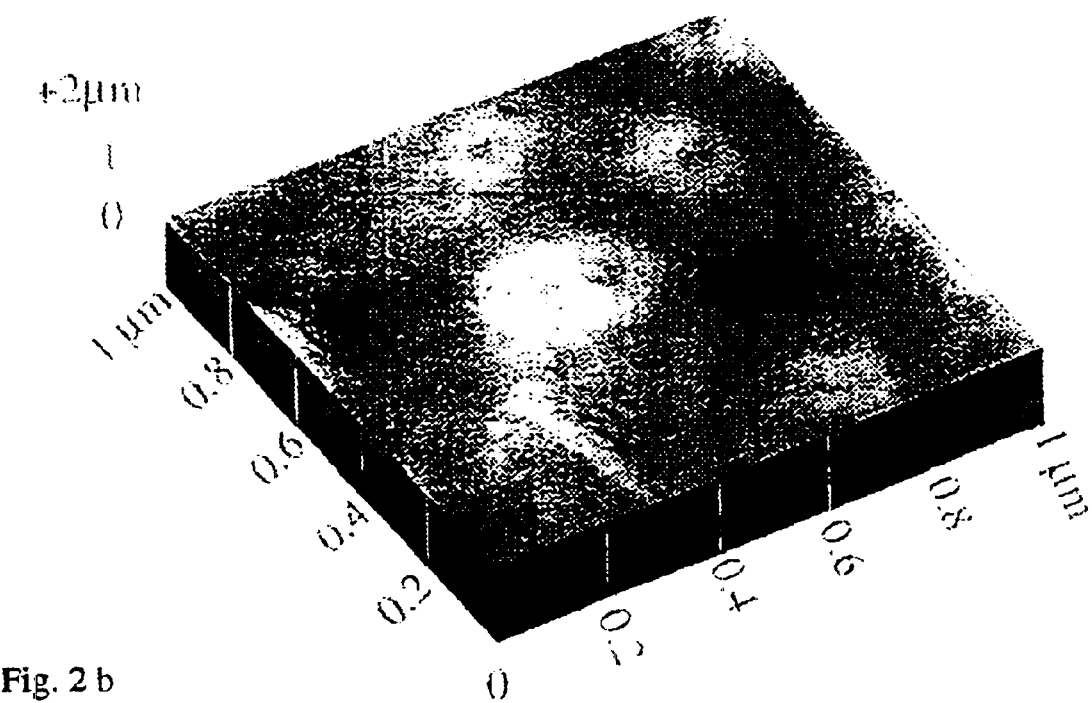
Figure 2:
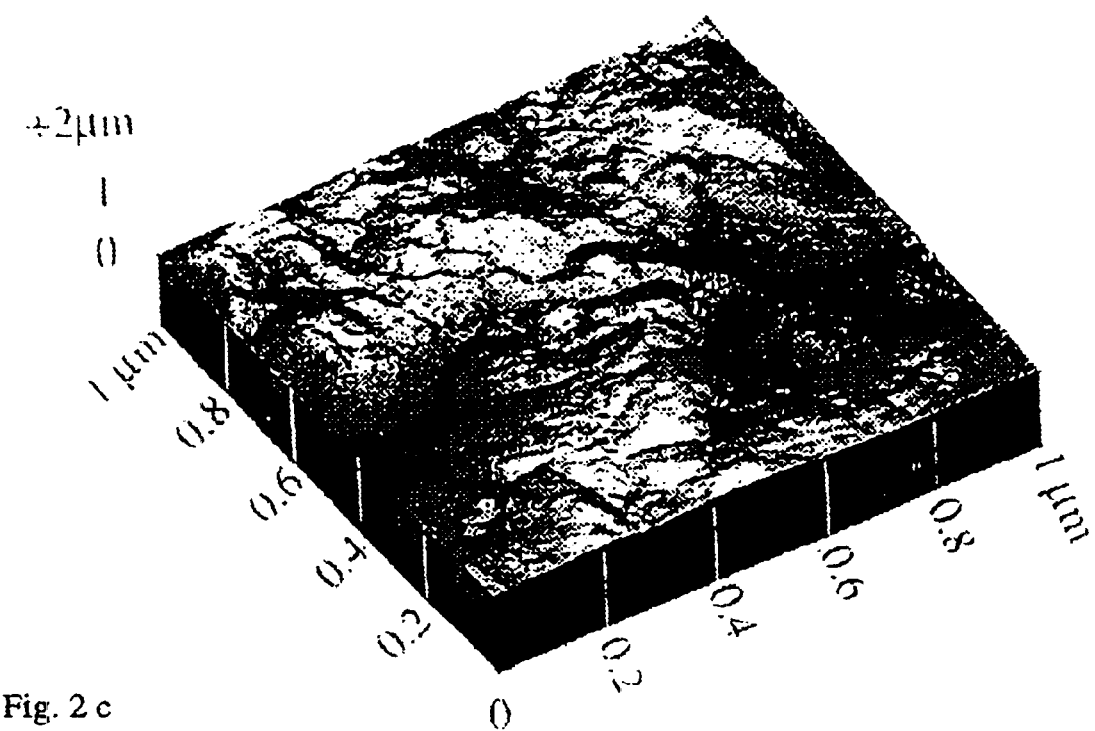

The machined (control) and machined plus anodized surfaces had a similar surface appearance with typical machining grooves in the width of 1–10 $\mu$m. The machined plus anodized surface also showed an additional, irregular surface roughness on the submicron level. The electropolished surface appeared very smooth whereas the electropolished plus anodized surface presented a heterogeneous surface with irregularly distributed smooth and rough (10–100 $\mu$m large) areas. No machining grooves were visible on the surfaces of the two groups of implants that had been electropolished. $R_{rms}$ values obtained by AFM are presented in Table I. Scanning electron micrographs are shown in FIG. 1 (electropolished+anodized implant, a–c; machined+anodized implant, d). AFM images are shown in FIG. 2 (electropolished+anodized implant a=rough part, b=smooth part; machined+anodized implant, c).

Paper V:

In this paper machined, glow discharge cleaned and thermally oxidized, glow discharge cleaned and nitrided and hydrogen peroxide treated implants were used. The machined (control) surface had the characteristic grooves, 1–10 $\mu$m in width as described above. The two groups which were plasma cleaned and subsequently oxidized and nitrided, respectively, had similar surface topography. The underlying grain structure could be seen although grooves from the machining procedure were clearly visible. The hydrogen peroxide treated implants showed clear traces from the machining procedure and had a woolly surface which reflects the etching action of the treatment.

Surface composition and thickness of surface layers

The results of the AES analyses are summarized in Table I.

Papers I, III

All samples had a relatively consistent surface composition independent of preparation. All spectra were dominated by strong Ti, O and C signals and trace amounts of Ca, S, Si, P, Cl and Na were detected. Ca and S appeared more frequently on the control samples than on the electrochemically prepared ones. Lower levels of C and other contaminants were found on the anodized (80V) samples. The depth profile analysis resulted in oxide thicknesses of 4, 4–5, 21, and 180 nm for the control, electropolished, electropolished/anodized (10V) and electropolished/anodized (80V) implants, respectively.

Papers II, IV

Irrespective of surface preparation all samples had a relatively similar surface composition with strong Ti, O and C signals in the spectra. The carbon contamination varied between the different samples from Å 34 at % for the machined and machined-anodized samples to Å 25 at % for the two electropolished samples. Trace amounts Ca, S, P, Si were detected (few percent).

Paper V

On all samples Ti, O or N/O and C were the dominant elements. All samples showed relatively low levels (10–15 at %) of carbon contamination on the surfaces compared to other studies (typically 30 at % or more) (Lausmaa J. 1996).

The oxides on the control, glow-discharge oxide and $H_2O_2$ treated samples respectively, were nearly stoichiometric titanium dioxide and of similar thickness (4–7 nm).

In Additional Experiments:

The disc-shaped implants used for studies on protein adsorption and inflammation in soft tissues consisted of a $TiO_2$ surface oxide covered by varying amounts of hydrocarbons and other trace impurities. For the machined control sample, carbon levels around 50%, and around 4% Ca and minor traces of S and P were detected. For the electropolished sample around 30% C was detected, and traces of Ca, S, and Cl. The electropolished plus anodized sample had carbon levels around 20%, and around 6% Ca and traces of S, Cl, Si and Fe. Except for the variations in carbon levels, the disc-shaped samples had a similar surface composition as the corresponding surfaces of threaded implants used in the previous studies (paper I–V).

Contact Angles and Surface Energy

The contact angles were measured on the circular disc-shaped implants since it is not possible to measure the contact angle on a screw-shaped implant (Table II and III).

The contact angle ($H_2O$ advancing) was lower for the electropolished plus anodized implant than for the machined and electropolished samples. Due to porosities of the electropolished plus anodized surface, capillary forces may spread the water, thus giving a lower water contact angle (Andrade, 1985). The electropolished plus anodized surface had the greatest hysteresis (difference between the advancing and receding angle) when measured with methylene iodide. Increased surface roughness and differences in topography may lead to increased hysteresis. Since all surfaces have a similar chemical composition, all surfaces will have the same "real" contact angle although the surface topography will influence the measured value.

The Tissue Response

Protein Adsorption in vitro

Our observations show that there are only small differences in the protein adsorption pattern between the machined, electropolished and electropolished plus anodized titanium surfaces. The total amount of adsorbed plasma proteins was similar on the three surfaces. The protein concentrations obtained were for machined titanium 1.15 mg/ml, electropolished titanium 1.05 mg/ml and electropolished plus anodized discs 1.25 mg/ml, respectively. Further, the content of selected plasma proteins, albumin, fibrinogen, fibronectin and IgG was similar.

Inflammatory Reaction in Soft Tissue.

Figure 3:
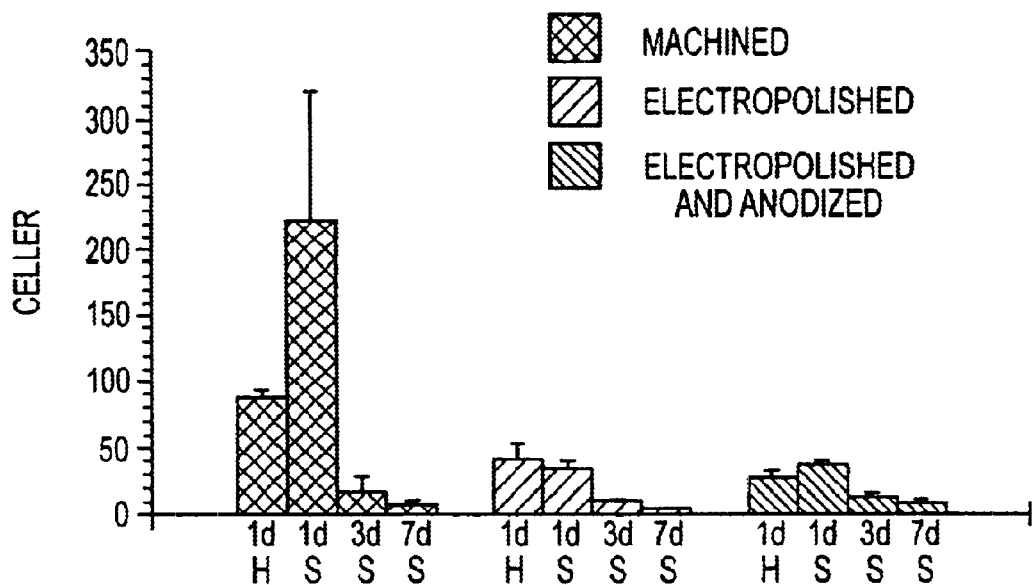
FIG. 3 is a graphical representation of the total number of cells in the exudates for each of the corresponding surfaces: machined; electropolished; and electropolished and anodized.
Figure 4:
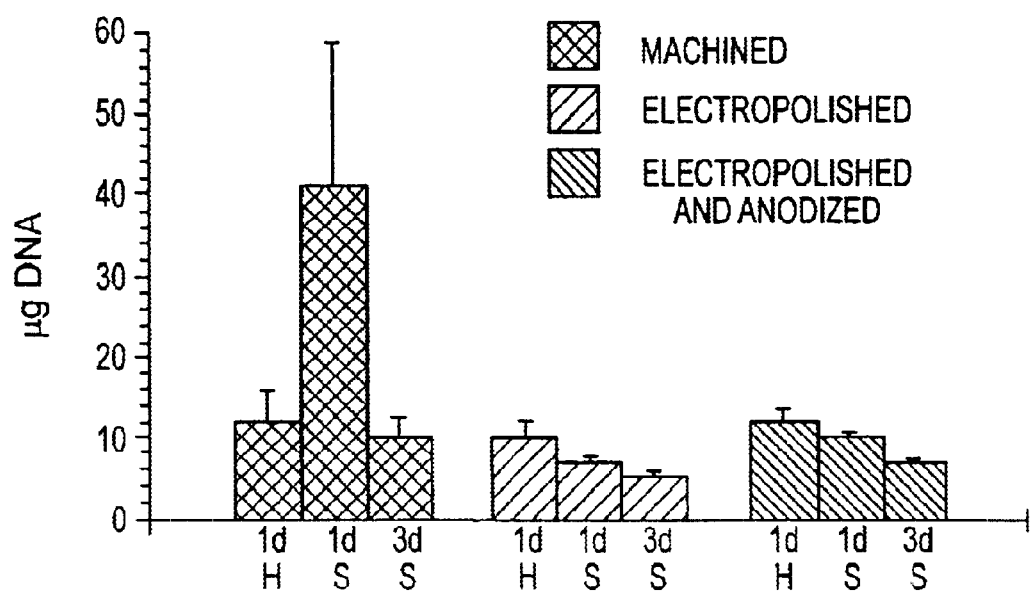
FIG. 4 is a graphical representation of the total amount of DNA associated with each of the corresponding surfaces: machined; electropolished; and electropolished and anodized.

The total number of cells in the exudates and associated with the surfaces of the machined, electropolished and electropolished plus anodized discs after different times of implantation are shown in FIGS. 3 and 4, respectively. The number of cells decreased with increasing observation periods at all implant types. No major differences in absolute total cell numbers were detected between the surfaces. Machined titanium pre-incubated in saline was one major exception revealing the highest cell numbers among all samples.

With one major exception, mononuclear cells (monocytes/macrophages, lymphocytes) were predominant in the exudates around the implants at all time periods (1 d: machined Ti 33% (HBSS) and 33% (saline), electropolished 47% (HBSS) and 50% (saline, electropolished plus anodized (47% (HBSS) and 55% (saline; 3 d: machined Ti 81% (saline), electropolished 87% (saline), electropolished plus anodized 82% (saline); 7 d: machined Ti 89% (saline), electropolished 100% (saline), electropolished plus anodized 94% (saline). In contrast to the other implants, machined titanium had a markedly lower proportion of mononuclear cells after 1 d, and a correspondingly higher proportion of PMN. This discrepancy was not observed at other time points. No difference in the proportion of cells in the exudate was observed between implants which had been incubated in HBSS or saline.

Morphology and Morphometry

Light Microscopic Observation

Paper I

After 7 weeks, immature bone with a wowen character filled the cortical threads around all implants. At this time period, the merely electropolished implants had less endosteal intramedullary downgrowth of the bone than the machined and the electropolished plus anodized (180 nm thick oxide) implants. The electropolished plus anodized implants had the highest bone contact, 50% versus 20%, for the merely electropolished. After 12 weeks, the general organization of the bone around the implants was the same as that observed after 7 weeks. only a small increase of the bone contact between 7 and 12 weeks were found for the electropolished plus anodized implants, however, for the two electropolished samples with a thin oxide the increased bone contact had reached the same level as the electropolished sample with thick oxide.

Papers II, IV

After 1 week the cortical bone was in general in close contact with the machined and machined/anodized implant types. Both the electropolished implant types had lower values for bone-implant contact at this time period (<5%).

At 3 weeks newly formed bone from the endosteum reached the implant and filled the threads which were initially protruding into the marrow cavity. No quantitative differences were detected between the groups.

Figure 5:
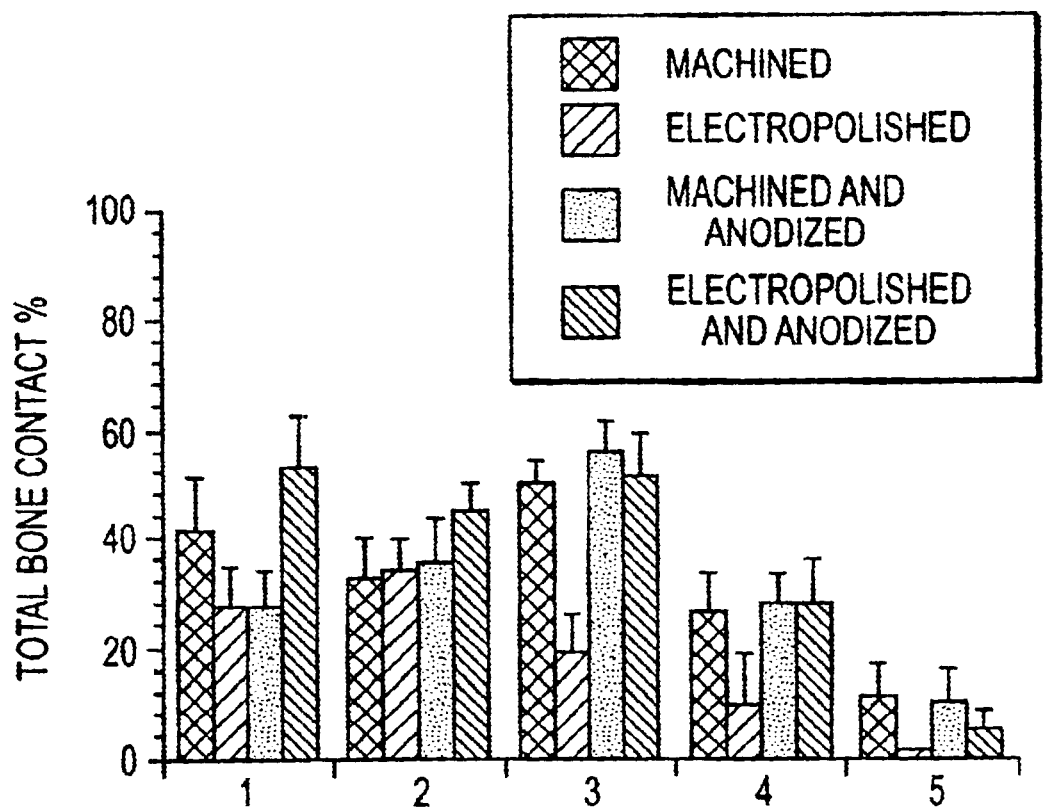
FIG. 5 is a graphical representation of total bone contact (%) in different threads after a 6-week implantation time.

At 6 weeks, the electropolished implant had a lower bone contact than the electropolished plus anodized implant as well as the machined implants FIG. 5. The electropolished implants also showed the lowest amount of bone within the threads. The two types of machined implants were surrounded by wider bone collar than the electropolished implants. In general, the bone was to a large extent in direct contact with the implant surfaces.

Figure 6:
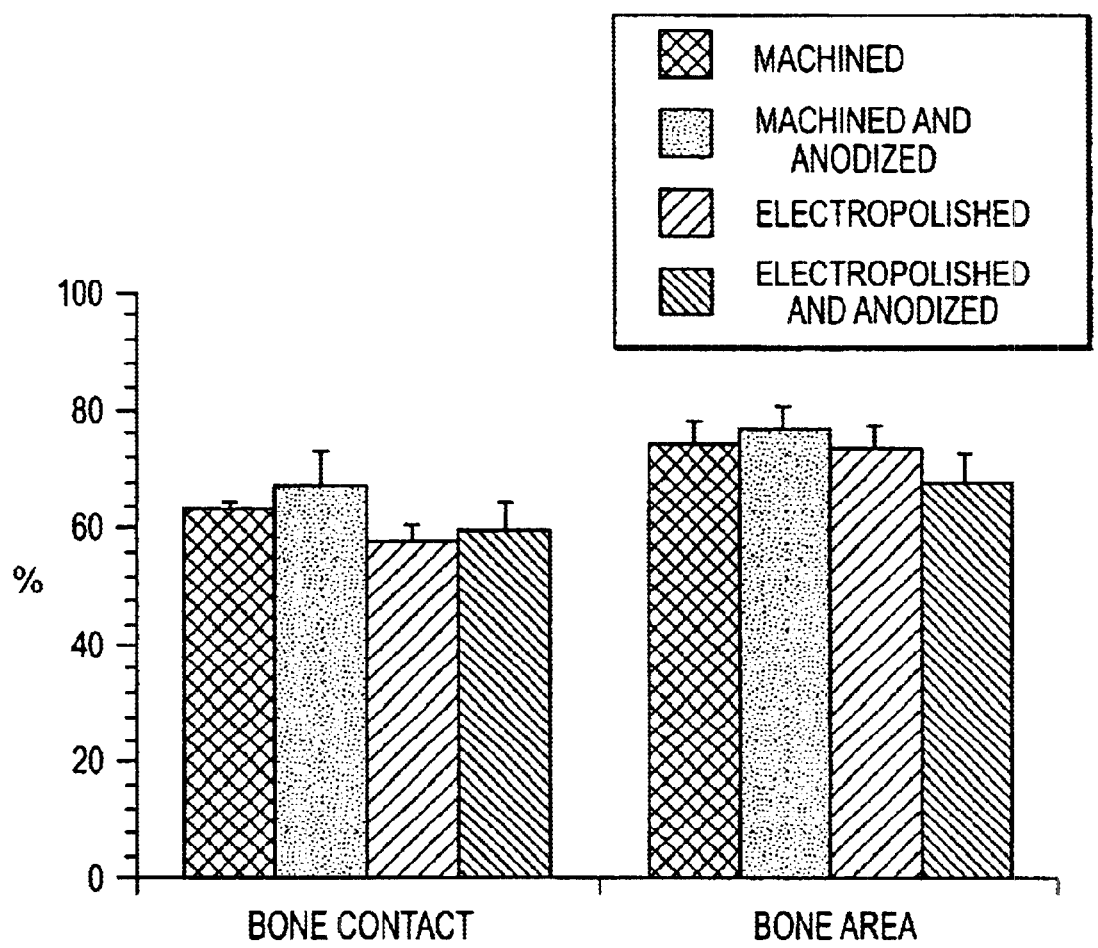
FIG. 6 is a graphical representation of total bone contact (%) in different threads after one-year implantation time.

After 1 year, almost all threads were filled with lamellar bone and the implant surfaces were in close contact with the surrounding bone (60–70%) (FIG. 6) The bone response to the different implant types were similar. The bone response around the electropolished implant group was equivalent with the other groups after one year.

Paper V

After 1 week the cortical bone was often in close contact with the implants although no new bone formation was seen at the cut edge of the cortex. No quantitative differences were seen between the groups.

At 3 weeks newly formed bone from the endosteum reached the implant and filled the threads which were initially occupied with marrow tissue. Marked signs of resorption and osteoid characterized the surface of the cortical and trabecular bone facing the implant surface. Also at this time point no differences in bone contact or bone area were detected between the groups.

At 6 weeks, no qualitative or quantitative differences were found between the groups. The bone was to a large extent in direct contact with the implant surfaces and these observations were similar to those detected in paper II.

Ultrastructural Observations

Paper III

A generally low degree of mineralization was found around the electropolished implants and together with the smooth fracture outline the production of ultrathin sections as well as the interpretation of the interface was made easier. There was constantly a layer of amorphous material between the mineralized bone and the implant surface (0.2 $\mu$m wide). The electropolished plus anodized implants (thick oxide) were more difficult to examine (similar for the machined implants) since a separation of the implant from the plastic embedded tissue often resulted in disruption of the interface tissue. The bone around the electropolished plus anodized implants had in general a much higher content of bone mineral than the merely electropolished implants. An amorphous layer was also found around these implants, generally somewhat thicker than for the merely electropolished implants. The presence of a lamina limitans forming the border of the mineralized bone towards the implant was usually found around the electropolished plus anodized implants with thick oxide.

Discussion

The relative importance of different surface properties for the biological performance of implanted biomaterials is largely unknown. The strategy chosen in the work was to systematically change the surface properties of titanium implants and then evulate the biological response in an animal model.

The surface chemistry, topography and microstructure of titanium surfaces have been varied in a well controlled manner in this thesis. There are several ways to modify the different properties although keeping all the parameters controlled is difficult.

Biocompatibility and Modified Titanium Surfaces

Implantation of a non-biological material in biological surroundings leads to a time- and partly material-dependent sequence of inflammatory and reparative processes, although, as reviewed in the Introduction, the various material-related factors that influence these responses are not fully understood it is evident that protein adsorption and cellular adhesion to material surfaces are essential components of the tissue responses. In previous studies in this laboratory (reviewed in the Introduction), the soft tissue reactions around machined titanium surfaces have been characterized, including the cellular distribution and structure of the titanium-metal interface in experimental and human applications.

In experimental studies in vivo and in different in vitro models, the surface wettability, chemical composition, pattern of protein adsorption and the influence of exogenous stimuli have been found to influence the inflammatory cell recruitment, distribution and secretory response. Further, on the background of an early (and transient) distribution of mononuclear and multinuclear cells on the machined titanium surface during the inflammatory events which precede bone formation in the interface (Sennerby et al., 1993a; Sennerby et al., 1993b) studies on protein adsorption and cellular recruitment and adhesion to surface-modified titanium implants were initiated.

The observation from the present experiment on in vitro plasma protein adsorption and cellular recruitment and adhesion in soft tissues of the rat indicate that no major differences were observed at a few selected time points, irrespective of the different surface properties exhibited by the machined, electropolished and electropolished titanium discs. We have no explanation for the relatively higher cell numbers on machined titanium after 1 day. In agreement with other recent observations (Thomsen et al., in manuscript), the machined titanium samples were associated with both a relatively greater influx and association of cells to the surfaces after 1 day then the other materials. Further, our data indicate that this inflammatory response is higher if implants are pre-incubated in saline than HBSS (with calcium). Moreover, the inflammatory exudate around the machined implants was associated with a markedly higher proportion of PMN. Interestingly, gold implants having less inflammatory cells in the exudate then hydroxylated and methylated gold, was associated with a similar, relatively greater PMN predominance after 1 day (Lindblad et al., 1997).

The present result together with previous experimental and clinical studies using machine implants in soft tissues, provide an indication that also the electropolished and electropolished plus anodized implants belong to a group of materials with soft tissue biocompatible properties.

The Osseointegration Process

The Osseointegration Process and Modified Titanium Surfaces

The systematic approach in papers I–V was undertaken with the purpose to evaluate if and how variations of the metal implant surface properties could induce a variation of the bone reactions, as evaluated by light microscopic morphometry and ultrastructural analysis. Thus, the thickness, morphology, topography and chemical composition of the surface layer could be more or less intentionally varied. Since the machined titanium constituted the implant on which surface modifications were made and, further, since a volume of scientific data exists on the material, biological and clinical properties of machined titanium implants, these implants were always included as a reference in the separate experiments.

In spite of the widespread use of machined titanium implants in bone, the mechanisms for achieving osseointegration has been less well understood. Previous experimental studies using the same experimental model as in this thesis (Sennerby et al., 1993a; Sennerby et al., 1993b) that the implant surface did not serve as an attachment for osteoblasts and no evidence was obtained indicating that mineralization was initiated on the surface: instead bone formation was observed after 3 days in the endosteum from which bone trabeculae projected towards the implant, and after 7 days as solitary islands within the threads. In both locations mineralization occurred by deposition of mineral in the collagenous matrix. Thus, the bone was growing towards the implant surface and the collageneous matrix of the interface zone was the last part of the surrounding bone to become mineralized. After longer time periods, observations from animal experiments and human retrieval studies (reviewed in the Introduction) indicate that osseointegration of non-functionally and functionally loaded machined, threaded titanium implants is characterized morphologically by a high amount of remodeled bone within the threads, a high bone-implant contact and a separation of mineralized bone from the implant surface by a thin zone of amorphous material.

In summary, the surface modified titanium implants evaluated in the present study (paper I–V) were found to essentially share biological properties with machined titanium: early bone formation proceeded towards the implant surface and at later time periods all implants were osseointegrated.

A major exception was the relatively low bone contact observed with electropolished implants in the early phase (papers I–II). A possible explanation for this observation could be the existence of an initial, larger gap between the electropolished implants and the surrounding tissue (due to the removal of less than 100 $\mu$m (Å50 $\mu$m) of the implant surface during the electrochemical process). However, the lower rate of bone formation around merely electropolished samples after 6 weeks in comparison with the electropolished plus anodized samples can not be explained by the difference in possible initial gap between the implant surface and the tissue. It is suggested that the combination of a heterogeneous submicron roughness (smooth/rough; 75%/25%), increased oxide thickness (180 nm) and thereby an increased crystallinity on the electropolished plus anodized surface are advantageous properties associated with the electropolished plus anodized implants. This combination of properties has not been utilized previosly as part of an implant element but reports in the litterature indicate that for instance the degree of crystallinity may (as a single property) affect cell behaviour.

In studies in vitro an increased crystallinity (while keeping oxide thickness and roughness parameters constant) was found to influence the phenotypic expression of osteoblasts (Boyan et al., 1995). In vitro studies have also shown that the roughness of the culture substratum influences osteoblast-like cell proliferation, differentiation and matrix production (Martin et al., 1995). Further, cells at different stages of differentiation in vitro respond differently to the same surface (Boyan et al., 1995; Schwartz et al., 1996). Therefore, if extrapolating to in vivo conditions it is possible that the titanium-bone interactions could be different at early and late time periods depending on time-dependent changes in the interface of the types of cells present and their maturity stage.

Although conflicting data exist in the literature, previous studies in vivo indicate that an increased surface roughness (on the >1 $\mu$m level) may promote bone adaptation to titanium surfaces (Buser et al., 1991; Goldberg et al., 1995; Gotfredsen et al., 1995). It is therefore interesting, on the basis of the present one year data (paper IV) that firstly, all surfaces (machined, machined plus anodized, electropolished, electropolished plus anodized), being relatively smooth compared to sandblasted or plasma sprayed surfaces exhibited a high degree of bone-to-implant contact and a high proportion of bone within threads, and secondly, that the morphometric values were equal to or higher than the values given for relatively rougher surfaces in another study using the same experimental model (Wennerberg, 1996). We have no clear explanation for these findings. One possibility is that the smooth electropolished surface had acquired a thicker oxide and thereby a changed topography during the longer implantation period (1 year). Some evidence that such processes may be operative is the finding, in human retrieval studies, that the thickness of the oxide had increased with time (Lausmaa, 1988; McQueen et al., 1982; Sundgren et al., 1986). Another possibility is that the rate of bone formation and mineralization around the machined and surface modified titanium implants was influenced by ion release. Titanium ions ($Ti^{4+}$) have a dose related inhibitory effect on calcification in vitro (Blumenthal and Cosma 1989). The ion release rates in vitro from titanium materials decay with time due to self passivation (Healey and Ducheyne, 1992a; Healey and Ducheyne, 1992b). Therefore, due to a relatively thinner oxide we cannot exclude that the electropolished implants are associated with a higher ion release.

Another hypothesis is that the titanium surface oxide, through its ability to bind calcium could favour mineralization, which in turn might be beneficial for bone formation (Hanawa, 1990). However, it has not been shown that this would have an effect on osteoblast adhesion, proliferation, secretion of extracellular matrix and mineralization of the titanium-interface zone. Previous in vivo data (Sennerby et al., 1993a; Sennerby et al., 1993b) and the present data (papers I–V) do not indicate that this is valid under the "vivo" conditions.

However, the anionic $TiO_2$ attracts cations, like for instance calcium, and it has been suggested that calcium binding may be one mechanism by which proteins adsorb to $TiO_2$ (similar to hydroxyapatite) (Ellingsen, 1991). Pre-treatment of $TiO_2$ by adsorption of lanthanum ions causes an increased adsorption of proteins, coinciding with an inferior bone response in rats and rabbits (Ellingsen and Pinholt, 1995). In addition, pre-treatment of titanium implants with fluoride ions has been shown to increase push-out values (Ellingsen, 1995). Thus, a chemical modification of the titanium surface may influence the bone tissue response, possibly by the adsorption of proteins to the surface. This hypothesis is mainly supported by in vitro studies which have shown that chondroitin-4-sulphate is bound to $TiO_2$ in the presence of calcium ions. Thus, tentatively in the amorphous zone, calcium bound to $TiO_2$ could promote the adsorption of sulphated glycosaminoglycans (Collis and Embery, 1992).

Taken together, chemical modifications of the titanium oxide surface have been found to affect the adsorption of macromolecules on the surface, and the tissue response. There are yet no evidence, however, that the positive effects on the bone response are due to a process of bone formation and mineralization which is directed outwards from the $TiO_2$-surface. A future approach with the purpose to further modulate the bone response may be to selectively adsorb/incorporate molecules to the surface which could influence bone precursor cells/osteoblasts and enhance mineralization. However, since the interactions between proteins, cells and such a chemically treated surface may be influenced not only by the chemical properties of the surface but also by the surface submicron roughness, an optimization of both chemical and surface roughness parameters have to be concidered when new implants are designed. The present invention is not limited to be used as an implant surface as such but may be utilized as a substrata for such purposes.

On the basis of available literature (reviewed above) and knowledge it may be concluded that the integration of titanium implants and bone and the maintenance of this integration are prerequisites for the clinically documented long-term function and high success rates. However, the kinetics of the process of osseointegration described above implies that the early phase of healing prior to adequate stability might be particularly crucial in situations with an inferior bone quality and other negative host factors. Experimental studies on threaded titanium implants in more or less compromised local implant beds (previous irradiation of tissues or local inflammation and osteopenia) support this assumption (Sennerby and Thomsen 1993; Öhrnell et al., 1997). Further, studies in patients with rheumatoid arthritis have shown a reduced mechanical capacity (decrease in torsional strength) of the bone-titanium unit in comparison with patients with osteoarthritis (Brånemark, 1996).

On the basis of the present results during the early phase of healing it is suggested that machined and electropolished c.p. titanium implants with poly-crystalline, thick oxides and a microporous roughness on the submicron level may be interesting materials to be evaluated under clinical conditions. However, it is apparent that also an adequate remodelling of bone around the implants is required in order to promote a long-term stability. It is therefore of interest that in our long-term (1 year) study (paper IV) the experimental results showed that all four types of threaded, titanium implants, irrespective of surface modification (machined, machined and anodized, electropolished, electropolished and anodized), had a high degree of bone-to-implant contact and a high proportion of mature, lamellar bone within threads. Thus, implants with a similar chemical composition but with marked differences in oxide thickness, surface topography and roughness, became equally well osseointegrated under long-term experimental conditions.

The examples given above have shown that it is possible to produce titanium implants with surface modifications which vary with respect to oxide thickness, composition, topography, roughness and microstructure. On the basis of results in thesis by Larsson (1997) it may be summarized that in comparison with the merely electropolished implants (which had a very smooth surface with a thin, non crystalline oxid) and machined implants, the implants which were surface modified with anodization aquired a thicker oxid (180–200 nm), increased crystallinity and increased roughness on the submicrometer scale.

A high degree of bone surrounding, and in contact with the implant, was found for all titanium implants, irrespective of surface modification. Taken together, the light microscopic, morphometric and ultrastructural observations indicate that the process of osseointegration is basically similar for machined and surface modified titanium implants.

The results of the biological experiment show that a combination of increased oxide thickness, oxide crystallinity and roughness on the submicrometer scale are advantageous properties for the early bone response, particularly in comparison with thin, smooth non-crystalline oxide surfaces.

A high degree of bone-to-implant contact and a high proportion of lamellar bone within the threads of the implants are observed after one year, irrespective of surface modification (machined, machined plus anodized, electropolished and electropolished plus anodized). The latter results indicate that the combination of surface properties (increased oxide thickness, increased crystallinity and roughness on the submicrometer scale) of anodized implants have equal long-term biological properties in bone as the clinically used machined titanium implants.

Taken together, our observations indicate that a titanium surface with a combination of surface properties (increased oxide thickness, increased crystallinity and roughness on the submicrometer scale), acquired in the present experiments by anodization, constitute an important element of implanted device.

TABLE I

Summary of the results from surface characterization of the implants.

| Preparation (paper) | Sterilization | Contamination at % | Oxide/nitride thickness (nm) | Rrms, (nm) | Adiff, % | Microstructure and oxide crystallinity |
|---|---|---|---|---|---|---|
| Machined (I, III) | steam sterilized | 45–80 at % C (Ca, S, Si, P, Cl and Na) | 4 | 29 | — | Plastically deformed, amorphous metal surface, non-crystalline oxide |
| Electropolished (I, III) | steam sterilized | 55–90 at % C (Ca, S, Si, P, Cl, and Na) | 4–5 | 2.7 | — | Polycrystalline metal surface, non-crystalline oxide |
| Electropolished + anodized, (I, III) | steam sterilized | 55–70 at % C (Ca, S, Si, and Cl) | 21 | 1.5 | — | Polycrystalline metal surface, non-crystalline oxide |
| Electropolished + anodized, (I, III) | steam sterilized | 34–40 at % C (Ca and Cl) | 180 | 16 | — | Polycrystalline metal surface. Partly rystalline oxide (anatase) |
| Machined (II, IV) | steam sterilized | 34.4 at % C, 1.7 at % Cl, 3.5 at % Na, (Ca, S, P, Si, and F) | 3–5 | 30.3 | 10.8 | Plastically deformed, amorphous metal surface, non-crystalline oxide |
| Machined + anodized, (II, IV) | steam sterilized | 33 at % C, 1.1 at % Na, (Ca, S, P, Cl, and Si) | 180–200 | 40.8 | 18.0 | Plastically deformed, amorphous metal surface, non-crystalline oxide |
| Electropolished (II, IV) | steam sterilized | 26.9 at % C, (Ca, S, Cl and Na) | 3–5 | 2.9 | 0.5 | Polycrystalline metal surface, non-crystalline oxide |
| Electropolished + anodized, (II, IV) | steam sterilized | 25.2 at % C (S, Ci and Na) | 180–200 | 32.3 / 2.7 (smooth) / 116.7 (rough) | 23.3 / 0.6 (smooth) / 88.0 (rough) | Polycrystalline metal surface Partly crystalline oxide |
| Machined (V) | γ-irradiated | 23 at % C (Ca, Si, S and Cl) | ≈3 | 26.3 | 13.1 | Plastically deformed, amorphous metal surface, non-crystalline oxide |
| Glow discharge cleaned and thermally oxidized (V) | γ-irradiated | 12 at % C (S) | ≈2 | 10.2 | 0.78 | Polycrystalline metal surface, non-crystalline oxide |
| Glow discharge cleaned and nitrided (V) | γ-irradiated | 10 at % 0 and C (Si) | TiN ≈ 3 | 25.2 | 8.63 | Polycrystalline metal surface, non-crystalline oxide |
| Hydrogen peroxide treated (V) | — | 12 at % C (Ba, Cl and Zn) | 7 | 25.6 | 20.5 | Plastically deformed, amorphous metal surface, Non-crystalline oxide |

TABLE II

The mean value for the three measurements (drops on one disc) are presented. The value for each drop (mean for right and left side of the drop) is presented within parentheses.

| Preparation | $H_2O$ advancing (contact angles) | $H_2O$ receding (contact angles) | $CH_2I_2$ advancing (contact angles) | $CH_2I_2$ receding (contact angles) |
|---|---|---|---|---|
| Machined | 41.2 (37, 44.5, 42) | — (18, <10, 13) | 47 (43, 46, 53) | 42 (39.5, 40.5, 45.5) |
| Electropolished | 39.5 (38.5, 37.5, 42.5) | — (12.5, 14.5, <10) | 35 (37.5, 32, 36.5) | 32 (31, 30.5, 33.5) |
| Electropolished and anodized | 22 (23, 22, 20.5) | <10 (<10, <10, <10) | 42.5 (45.5, 38.5, 43.5) | 32 (35, 32.5, 29) |

TABLE III

The surface energy for the different samples.

| Preparation | Surface energy dyne/cm | Polar component | Dispersion component |
|---|---|---|---|
| Machined | 58.1 | 33.6 | 24.4 |
| Electropolished | 61.3 | 32.2 | 29.1 |
| Electropolished and anodized | 68.6 | 42.8 | 25.8 |

What is claimed is:

1. An implant element for permanent anchorage in bone tissue said element having at least one surface intended to face the tissue, wherein said surface comprises titanium, wherein said titanium surface is modified by hydrogen peroxide oxidation to acquire a titanium oxide coating that has a carbon content from 10 to 15 atom percent.

2. An implant element according to claim 1, wherein the surface oxide crystallinity is altered to a polycrystalline structure.

3. An implant element according to claim 2, wherein the ratio between the smooth and rough areas is larger than 1.

4. An implant element according to claim 3 wherein the ratio between the smooth and rough areas is about 3.

5. An implant element according to claim 2, wherein the rough areas are between 10×10 μm and 100×100 μm.

6. An implant element according to claim 1, wherein the modified surface is a heterogenous surface with irregularly distributed smooth and rough areas.

7. An implant element according to claim 1 wherein said titanium oxide coating has a thickness from 2 to 7 nm, as measured by Auger electron spectroscopy depth profile analysis.

8. An implant element according to claim 1 wherein the carbon content is about 12 atom percent.

* * * * *